United States Patent [19]
Chapman et al.

[11] Patent Number: 5,201,735
[45] Date of Patent: * Apr. 13, 1993

[54] APPARATUS AND METHOD FOR TREATING A FRACTURE

[75] Inventors: Michael W. Chapman, Sacramento, Calif.; Dana C. Mears, Pittsburgh, Pa.; Charles C. Edwards, Baltimore, Md.

[73] Assignee: Pfizer Hospital Products Group, Inc., New York, N.Y.

[*] Notice: The portion of the term of this patent subsequent to Nov. 19, 2008 has been disclaimed.

[21] Appl. No.: 664,160

[22] Filed: Mar. 4, 1991

Related U.S. Application Data

[62] Division of Ser. No. 305,840, Feb. 2, 1989, Pat. No. 5,066,296.

[51] Int. Cl.$^5$ .............................................. A61F 5/04
[52] U.S. Cl. .................................... 606/67; 606/62; 606/63; 606/64
[58] Field of Search .................................... 606/60-68

[56] References Cited

U.S. PATENT DOCUMENTS

| | | |
|---|---|---|
| 3,334,624 | 8/1967 | Schneider . |
| 3,433,220 | 3/1969 | Zickel . |
| 3,977,398 | 8/1976 | Burstein . |
| 4,227,518 | 10/1980 | Aginsky . |
| 4,475,545 | 10/1984 | Ender . |
| 4,483,335 | 11/1984 | Tornier .................. 606/64 |
| 4,503,847 | 3/1985 | Mouradian .............. 606/64 |
| 4,522,202 | 6/1985 | Otte et al. . |
| 4,622,959 | 11/1986 | Marcus . |
| 4,697,585 | 10/1987 | Williams . |
| 4,705,027 | 11/1987 | Klaue . |
| 4,733,654 | 5/1988 | Marino . |
| 4,805,607 | 2/1989 | Engelhardt et al. . |

OTHER PUBLICATIONS

Allen et al., "A Fluted Femoral Intramedullary Rod; Biomechanical Analysis and Preliminary Clinical Results:, Jour. Bone and Joint Surgery", vol. 60-A, No. 4, pp. 506-515 (Jun. 1978).
Sampson Corp., "Fluted Intramedullary Rod System" brochure (1974).
Gross & Kempf, "Intramedullary Nailing System," Howmedica, Inc. 1983 and 1984.
Russell-Taylor, "Tibial Interlocking Nail Systems," Richards.
"Brooker Tibial System," Biomet, Inc.
"Brooker Tibial Nail Surgical Technique," Biomet, Inc.
Taylor et al., "Surgical Technique-Delta Tibial System".
Gustilo, R. B., M. D. and Chapman, M. W., M.D., "Orthopedic Surgery Viewpoint '83, Management of Type III Open Fractures", Eli Lilly & Company.

Primary Examiner—Robert A. Hafer
Assistant Examiner—Kerry Owens
Attorney, Agent, or Firm—Pennie & Edmonds

[57] ABSTRACT

Apparatus for fixing a fracture of a bone including an elongated body member having a proximal end and a distal end for insertion into the intramedullary canal of the bone; a tab member having at least one aperture to allow for passage of a screw for fastening of the tab member to the bone; and a bolt for selectively removably coupling the tab member to the proximal end of the body member. Preferably, the tab member is of a hollow cylindrical configuration and removably interlocking the first plate member to a second plate member. In another embodiment, the apparatus include a body member for insertion into a bone cavity, the body member having at least one aperture disposed in close proximity to its first end to allow for passage of a screw for fastening the body member to the bone. The present invention is also directed to apparatus for fixing a bone fracture including a first elongated plate member having at least one aperture so as to permit passage of a screw for attachment to the outer surface of a first portion of the bone. The first plate member has a first end and a second end and has a predetermined curvature so as to conform generally to the curvature of the first portion of the bone. The apparatus includes a second elongated plate member having a predetermined curvature so as to conform generally to the curvature of the second portion of the bone. A C-shaped channel is disposed on the first end of the first plate member for selectively removably interlocking the first plate member to the second plate member.

16 Claims, 5 Drawing Sheets

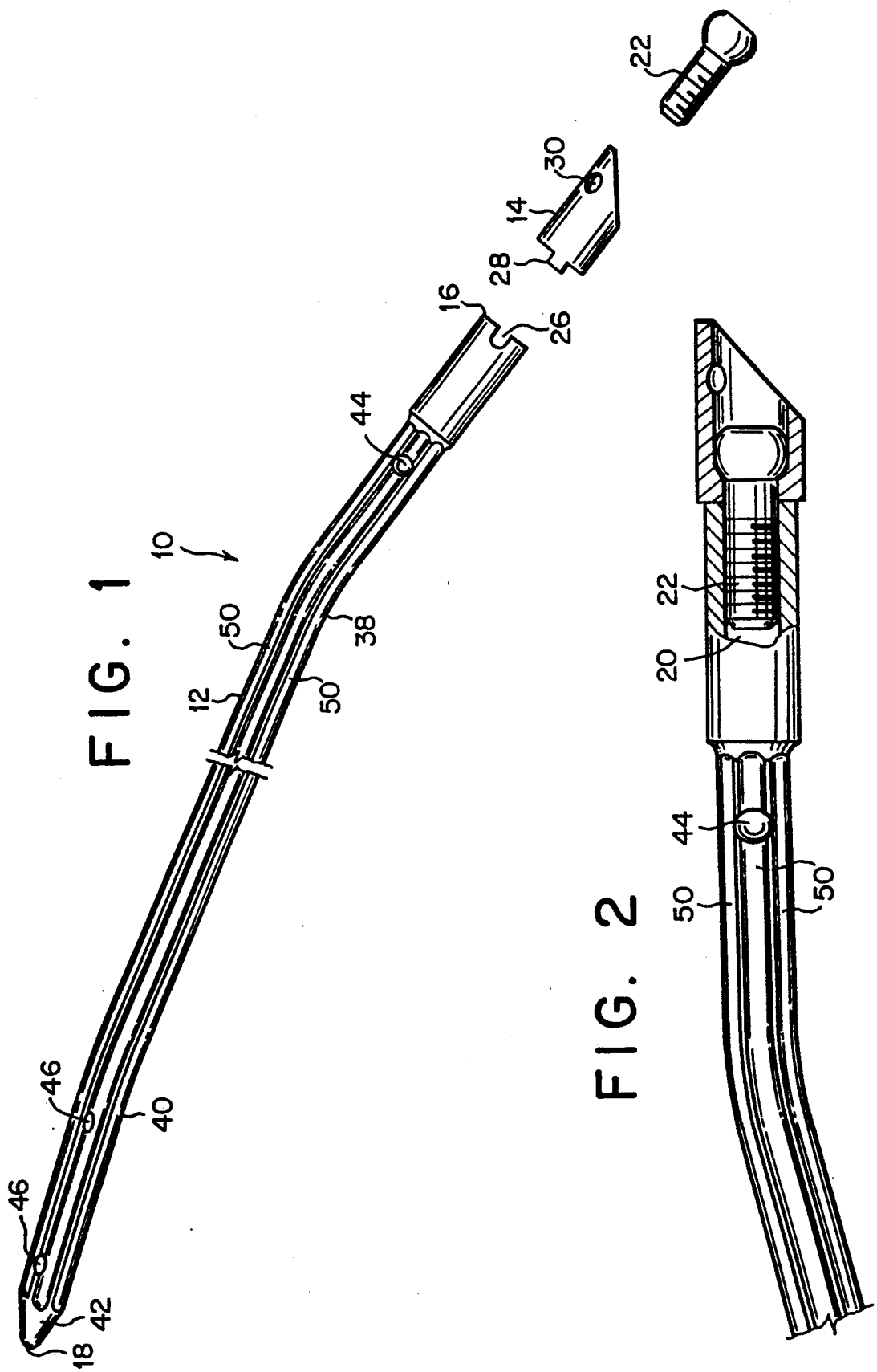

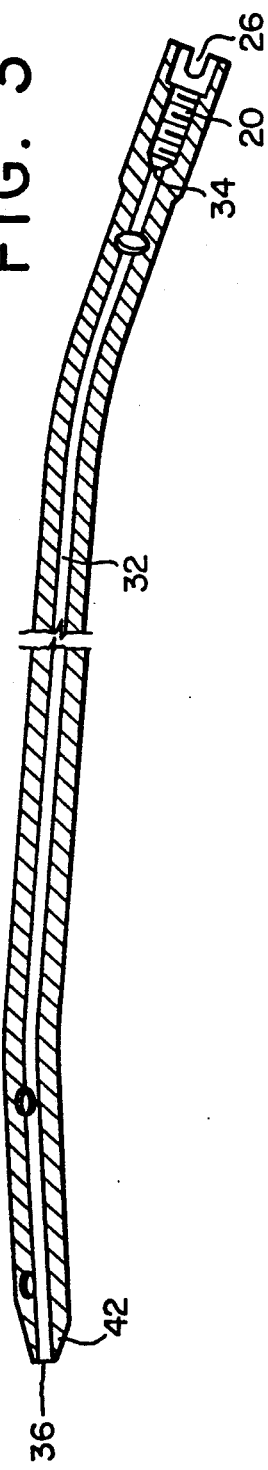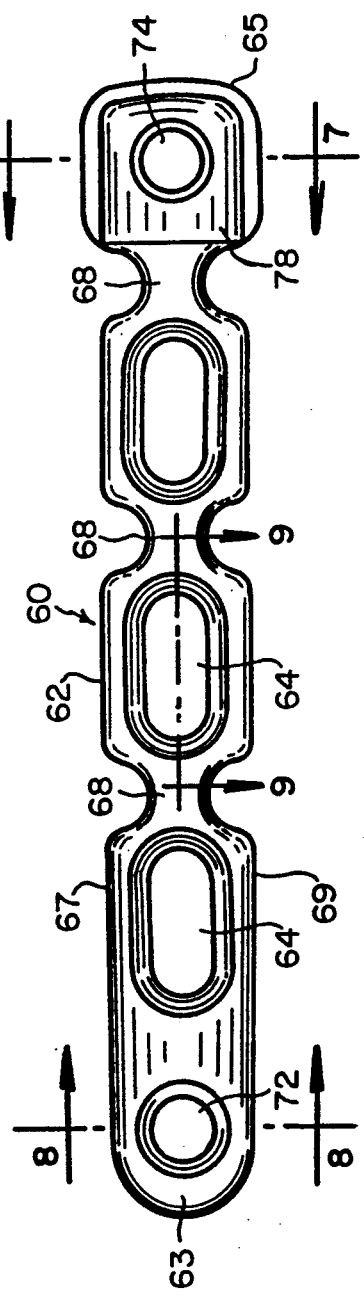

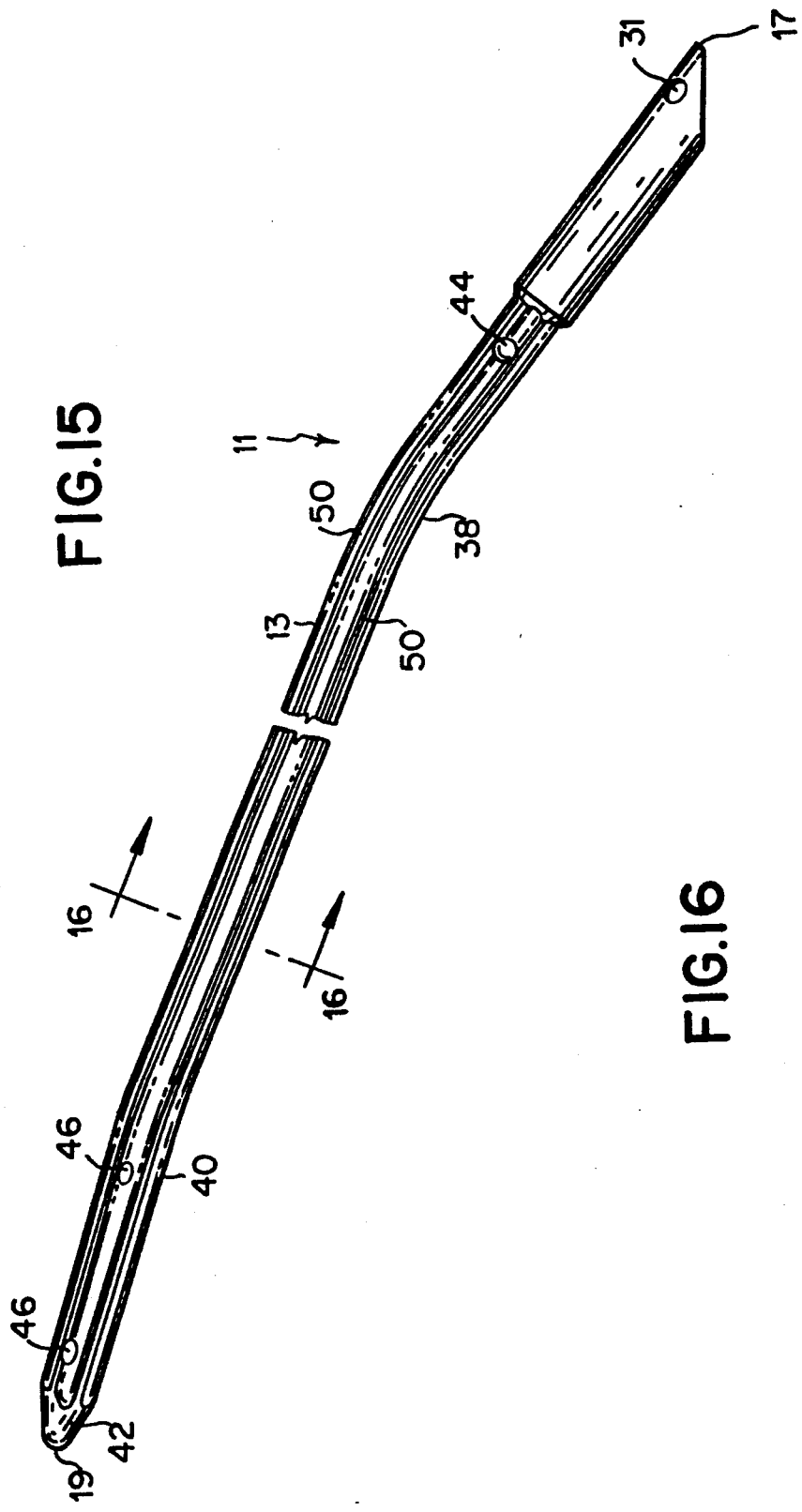
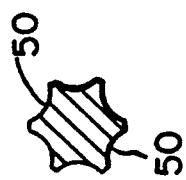

APPARATUS AND METHOD FOR TREATING A FRACTURE

This is a division of application Ser. No. 07/305,840, filed Feb. 2, 1989, now U.S. Pat. No. 5,066,296.

FIELD OF THE INVENTION

The present invention relates to devices and methods for treating a fractured bone. In particular, the present invention is directed to an intramedullary rod directed to the treatment of a bone fracture, for example, in the tibia and humerus, and also to plates for use, for example, on the pelvis, fibula, forearm and distal humerus.

BACKGROUND OF THE INVENTION

The utilization of intramedullary nails or rods in the treatment of bone fractures is well known in the art. Furthermore, a number of prior art intramedullary nail systems comprise intramedullary nails provided with holes therethrough adjacent the proximal and distal ends for insertion of locking screws. Depending upon the severity of the fracture, the intramedullary nail may be implanted without locking screws, with at least one locking screw either proximally or distally (known as either partial or dynamic locking) or with at least one locking screw both proximally and distally (known as either complete or static locking).

Static locking neutralizes rotational stresses while preventing shortening of the limb. Dynamic locking neutralizes rotational stresses on one side of the fracture site while permitting axial loading. A static locking condition may be converted into a dynamic locking condition by removing either the proximal or distal screws, thereby permitting axial loading. Both a dynamic locking condition and static locking condition may be converted into an unlocked condition by removing all locking screws, thereby allowing rotational stresses across the fracture site and allowing axial loading of the fracture site.

When properly permitted, rotational stresses and axial loading, combined with patient weightbearing, enhances the healing process. However, the removal of the locking screws has the severely adverse effect of permitting the intramedullary nail to migrate or back out of the intramedullary canal.

Prior art devices for treating a bone fracture further include plates with holes therethrough for screws to be inserted. These plates are designed to impart compressive forces on the fracture site. A plate, known as a tension band plate, may be applied to one side of the fractured bone with a tension device, and secured with a number of screws which are inserted through the bone and which firmly attach the plate. A tension band plate applies compressive forces to the fracture site and resists rotational stress.

In some round bones there is not enough room to apply the tension device. In such instances a semi-tubular plate with oval holes therethrough for screws to be inserted may be utilized. When screwed firmly to the bone, the edges of the semi-tubular plate press into the cortex and resist rotation. When screws are inserted eccentrically at one end of the oval, the plate is placed under tension as the spherical head of the screw engages the plate. Standard size prior art semi-tubular plates, for example, are made with oval holes which accept a single 4.5 mm cortex screw, while small plates accept one 3.5 mm cortex screw. Semi-tubular plates may be bent and twisted so as to fit the fractured bone. If it is necessary to use more than one plate, they can be applied adjacent one another but without any cooperating engagement between them.

Further detail review of such prior art devices are presented in the following publications which are incorporated herein: "The Grosse & Kempf TM Intramedullary Nailing System", Howmedica, Inc., 1983 and 1984; Boyle, Marc, M.D., "Howmedica TM Surgical Techniques—Grosse & Kempf TM Surgical Technique", Howmedica, Inc., 1984; "Russell-Taylor Tibial Interlocking Nail Systems", Richards; "Brooker Tibial System" and "Brooker Tibial Nail Surgical Technique", Biomet Inc.; "Howmedica Quality Systems, The Howmedica ICS TM Stainless Steel Compression Systems", Howmedica, Inc., 1980; Ramon B. Gustilo, M.D. and Michael W. Chapman, M.D., "Orthopedic Surgery Viewpoints '83, Management of Type III Open Fractures", Eli Lilly and Company; "ECT European Compression Technique, Internal Fracture Fixation Reference Manual", Zimmer, Inc.; "Osteo Auto-Compression Plating System Catalog", Richards Medical Company, 1985; "ORIF", DePuy, Inc., 1986; "Introducing Two New Small Bone Sets From Synthes", Synthes Ltd., 1986; and "ASIF Technique", Synthes Ltd.

SUMMARY OF THE INVENTION

The present invention is directed to an apparatus comprising a body member for insertion into a bone cavity, the body member having a first end and a second end; a tab member having at least one aperture to allow for passage of a screw for fastening the tab member to the bone; and means for selectively removably coupling the tab member to the first end of the body member.

According to one preferred embodiment, the tab member is generally of an annular configuration and has a first end for coupling with the first end of the body member. Its other end is beveled. The one aperture is disposed adjacent the beveled end. Preferably, the tab member has at least one protrusion and the body member has at least one recess configured and dimensioned so as to removably engage the protrusion. Also the body member has a bore at the first end. The bore is configured and dimensioned for engagement with a means for inserting and removing the body member from the bone cavity. This bore is threaded and the coupling means is a bolt disposed on the tab member and being configured and dimensioned for engagement with the bore.

The present invention is also directed to an apparatus for fixing a fracture of a bone comprising elongated body member for insertion into the intramedullary canal of the bone, the body member having a proximal end and a distal end; tab member having at least one aperture to allow for passage of a screw for fastening of the tab member to the bone; and means for selectively removably coupling the tab member to the proximal end of the body member.

Preferably, the tab member and the aperture are configured and dimensioned so as to allow access to the aperture when the body member is disposed in the bone cavity and the tab member is selectively coupled to the body member. The tab member is generally of a hollow cylindrical configuration and has a distal end for coupling with the proximal end of the body member. Also, the tab member has two equally spaced apart protrusions disposed on its distal end and the body member has two equally spaced apart recesses disposed on the proximal end and which are configured and dimensioned so as to removably engage the protrusions respectively.

In one preferred embodiment, the body member has a bore at the first end and the bore is configured and dimensioned for engagement with a means for inserting and removing the body member from the intramedullary canal. The bore is threaded and the coupling means is a bolt configured and dimensioned for seating within the hollow cylindrical tab member and for engaging with the bore so as to couple the tab member to the body member.

The body member preferably has a first bend adjacent the proximal end of the body member and has a second bend adjacent the distal end of the body member. Also, the body member has at least one aperture generally transversely therethrough disposed between the first bend and the proximal end of the body member. In addition, the body member has at least one aperture generally transversely therethrough disposed between the second bend and the distal end of the body member. At least one ridge is disposed longitudinally along the outer surface of the body member. The body member and tab member are each formed of titanium or a titanium alloy. The body member has an axial passageway and is open ended for selective passage of a guide wire therethrough. The body member also has a beveled portion adjacent its distal end.

The present invention is also directed to an apparatus comprising a body member for insertion into a bone cavity wherein the body member has at least one aperture disposed in close proximity to its first end to allow for passage of a screw for fastening the body member to the bone.

The present invention is further directed to an apparatus for fixing a bone fracture comprising a first elongated plate member having at least one aperture so as to permit passage of a screw for attachment to the outer surface of a bone. The first plate member has a first end and a second end and has means disposed at the first end for at least selectively removably interlocking the first plate member to a second plate member.

In an alternative embodiment according to the present invention, an apparatus for fixing a bone fracture comprises first elongated plate member having at least one aperture so as to permit passage of a screw for attachment to the outer surface of a first portion of the bone, the first plate member having a first end and a second end and having a predetermined curvature so as to conform generally to the curvature of the first portion of the bone; second elongated plate member having a predetermined curvature so as to conform generally to the curvature of the second portion of the bone; and means disposed on the first end of the first plate member for selectively removably interlocking the first plate member to the second plate member.

The interlocking means comprises a C-shaped channel portion configured and dimensioned for interlockingly receiving a correspondingly configured and dimensioned portion of the second plate member. The second plate member has a hole so as to permit passage of a screw for attachment to the outer surface of the second portion of the bone and the aperture of the first plate member is positioned in the C-shaped channel portion so as to overlay the hole in the second plate member plate portion when the first plate member is interlocked with the second plate member. Preferably the aperture and the hole are each at least one of a circular and oval configuration.

In an alternative preferred embodiment, first plate member includes a plurality of apertures and the second plate member includes a plurality of holes which apertures and holes are at least one of a circular and oval configuration. Also, the second end of the first plate member is one of a T and an H-shaped configuration.

BRIEF DESCRIPTION OF THE DRAWINGS

FIG. 1 is an exploded broken side view illustrating a tibial intramedullary nail, a locking tab member and a driver cavity bolt according to the present invention.

FIG. 2 is a partial enlarged side view partially in cross-section of the tibial intramedullary nail, locking tab member, driver cavity and driver cavity bolt as illustrated in FIG. 1.

FIG. 3 is a broken cross-sectional side view of the tibial intramedullary nail of FIG. 1 illustrating the driver cavity and interior canal.

FIG. 4 is a rear view of the locking tab member of FIG. 1.

FIG. 5 is a cross-sectional side view of the locking tab member of FIG. 1.

FIG. 6 is a top view of a tibial plate according to the present invention.

FIG. 15 is a broken side view illustrating a tibial intramedullary nail according to the present invention.

FIG. 16 is a cross-sectional view taken along line 16—16 of FIG. 15.

DETAILED DESCRIPTION OF THE INVENTION

Figure 9:
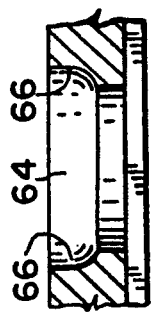
FIG. 9 is a cross-sectional view along line 9—9 of FIG. 6.

In the description which follows, any reference to either size, length, orientation or direction is intended primarily for the purpose of illustration and is not intended in any way as a limitation of the scope of the present invention.

While it is presently contemplated that in its preferred embodiment the locking tab member according to the present invention is directed to a tibial or humeral intramedullary nail, the present invention is not limited to use with a tibial intramedullary nail but may be used with a prosthetic implant of any type. As a matter of convenience, the invention will be described herein in reference to a tibial or humeral intramedullary nail.

Referring to FIG. 1, a tibial or humeral intramedullary nail 10 according to the present invention is illustrated. The tibial intramedullary nail 10 includes body member 12 for insertion into the intramedullary canal of a tibia for treatment of a fracture of the tibia. Locking tab member 14 which is of a generally annular configuration as shown in FIG. 2 is provided for selectively removable engagement with body member 12. Body member 12 has a first or proximal end 16 and a second or distal end 18. Body member 12 and locking tab member 14 can be selectively coupled by bolt 22 as shown in FIG. 2.

As illustrated in FIGS. 1-3, the first or proximal end 16 of body member 12 has a threaded driver cavity or bore 20 into which bolt 22 can be threaded. As shown in FIGS. 2 and 5, the locking tab member 14 has an aperture 24 through which bolt 22 can pass. Tab aperture 24 is configured and dimensioned so as to removably engage bolt 22 so that the locking tab member 14 can be selectively removably attachable to the proximal end 16 of body member 12 as shown in FIG. 2. According to the preferred embodiment, body member 12 has two equally spaced apart recesses 26, which can receive two correspondingly equally spaced apart locking tab protrusions 28 on tab member 14, as illustrated in FIGS. 1 and 3-5.

As shown in FIG. 4, locking tab member 14 is provided with two locking tab apertures 30. As illustrated in FIG. 1, locking tab member 14 and locking tab apertures 30 are configured and dimensioned so as to allow for passage of a single straight locking tab screw through either of locking tab apertures 30 to secure the locking tab member to a predetermined portion of the tibia. Locking tab member 14 and locking tab apertures 30 are further configured and dimensioned so as to allow access to either locking tab aperture 30 when the first end 16 and the second end 18 of body member 12 are disposed within the intramedullary canal of the tibia and the locking tab member 14 is engaged with the body member 12.

The present invention therefore allows a surgeon to insert a bone screw through either locking tab aperture 30 depending on whether the left or right tibia is fractured without the use of instrumentation and guides which would be necessary to insert a screw through a nonvisible aperture in a portion of body member 12 within the intramedullary canal. Furthermore, no additional incisions are required to insert a bone screw through either locking tab aperture 30 which presents a simple procedure whereby a surgeon can prevent an otherwise unlocked body member 12 from backing out of the intramedullary canal as well as reduce rotational stresses at the fracture site.

When locking tab 14 is not attached to body member 12, a driver (not shown) for inserting and removing the body member 12 from the intramedullary canal of the tibia can be utilized. The driver is provided with a first end which is threaded and is configured and dimensioned so as to threadedly engage driver cavity or bore 20 of body member 12. Alternatively, the first end of the driver can be provided with two driver protrusions which are configured and dimensioned so as to removably engage the two recesses 26 provided on first end 16 of body member 12.

The body member 12 according to the present invention can be provided in nominal outer diameter sizes ranging from 6 millimeters to 14 millimeters in 1 millimeter increments. The smaller sizes, such as 6 millimeters through 9 millimeters nominal outside diameter, are intended for insertion into a non-reamed intramedullary canal and do not require the use of a guide wire. Larger sizes, such as 10 millimeters through 14 millimeters nominal outside diameter, are intended for insertion into a reamed intramedullary canal and do require the use of a guide wire (not shown). As illustrated in FIG. 3, in the larger sizes the body member 12 is provided with an interior canal or axial passageway 32 having an interior canal entrance 34 located in driver cavity or bore 20 and an interior canal exit 36 located at second end 18 of body member 12. The interior canal accommodates the passage of the guide wire therethrough according to well-known procedures.

The body member 12 is provided with a first bend 38 and a second bend 40, as shown in FIG. 1. The first bend 38 is nearer the first end 16 and the second bend 40 is nearer the second end 18. First bend 38 is preferably located approximately 1 ¼ inches to 2 inches from first end 16, and causes the portion of body member 12 from first bend 38 to first end 16 to be bent approximately 15° in the anterior direction when body member 12 is located within the tibial intramedullary canal. Second bend 40 is preferably located approximately 1 ⅞ inches to 1 13/16 inches from second end 18, and causes the portion of body member 12 from second end 18 to second bend 40 to be bent approximately 6° in the anterior direction when body member 12 is located within the tibial intramedullary canal. The first and second bends 38 and 40 cause a reduction in the pressure applied to the posterior wall of the intramedullary canal when inserting body member 12 therein and facilitate manipulation of body member 12 during such insertion. To further diminish impingement of second end 18 against the posteror wall of the intramedullary canal, body member 12 is provided with a beveled portion 42 adjacent second end 18, as shown in FIG. 1. When body member 12 is provided with an interior canal 32, interior canal exit 36 is located in beveled portion 42, as illustrated in FIG. 3.

In the 8 millimeter and 9 millimeter nominal outer diameter sizes, body member 12 is preferably provided with a first proximal aperture 44 located between the first bend 38 and firs tend 16 and extending in the medial to lateral direction when body member 12 is disposed within the intramedullary canal. In the 10 millimeter nominal outer diameter size and larger sizes, body member 12 is preferably also provided with a second proximal aperture (not shown) located between first bend 38 and first proximal aperture 44 and extending in the anterior to posterior direction.

In the 8 millimeter and 9 millimeter nominal outer diameter sizes, body member 12 is preferably also provided with first and second distal apertures 46 located between second bend 40 and second end 18 and extending substantially in the medial to lateral direction when body member 12 is disposed within the intramedullary canal. In the 10 millimeter nominal outer diameter size and larger sizes, body member 12 is preferably also provided with a third distal aperture located between first and second distal apertures 46 and extending in the anterior to posterior direction.

As shown in FIGS. 1 and 16, body member 12 is provided with six ridges 50, each extending from a predetermined location between first proximal aperture 44 and driver cavity 20 to beveled portion 42 at second end 18.

The tibial intramedullary nail 10 according to the present invention can be made from any substantially rigid biocompatible material and is preferably made of metal. The preferred material of composition is titanium or a titanium alloy since the pliability of this metal in conjunction with the configuration and dimensions of body member 12 greatly diminish the force exerted on the posterior portions of the tibia by impingement of body member 12 thereon during insertion of body member 12 into the intramedullary canal.

According to the present invention, the nail 10 can be secured to the bone by a screw passing through either of apertures 30 in tab member 14 when the body member is positioned in the bone cavity without the need to pass screws through any of nail apertures 44 or 46.

Referring to FIG. 15, in another preferred embodiment of the present invention the nail 11 includes body member 13 having a first or proximal end 17 and a second or distal and 19. Body member 13 is provided with two apertures 31 which are disposed in close proximity to first end 17 and are spaced in relation to each other identically as shown for locking tab apertures 30 in FIG. 4. The body member 13 and apertures 31 are configured and dimensioned so as to allow for passage of a locking screw through either of apertures 31 to secure body member 13 to a predetermined portion of the bone. The first end 17 of body member 13 is of an annular configuration and is bevelled. The embodiment illustrated in FIG. 15 is similar to the above-described embodiment shown in FIG. 1, except for the absence of a separately distinct tab member 14 and means for selectively removably coupling the tab member to the first end of the body member. The embodiment shown in FIG. 15 essentially integrates tab member 14, shown in FIG. 1, with body member 12, resulting in body member 13.

While it is presently contemplated that the preferred embodiments of the plates configured and dimensioned according to the present invention are intended for use in treating fractures of the tibial shaft, the medial tibial plateau, the lateral tibial plateau, the distal anteromedial tibial epiphysis, the fibula, the forearm, the distal humerus and the pelvis, the present invention is not limited to plates for treating fractures of the above-identified bones but may be used for treating fractures of any bone. As a matter of convenience, the description of the preferred embodiment of the bone plates will refer to the device as a tibial plate.

Referring to FIG. 6, the tibial plate 60 according to the present invention has a body or plate member 62 which has a plurality of circular or oval apertures therethrough and a first end 63, a second end 65, a first side 67 and a second side 69. Plate member 62 is provided with at least one and preferably several substantially oval shaped apertures 64 which are configured and dimensioned so as to removably engage the heads of either one substantially hemispherical headed 5 millimeter screw or two parallel substantially hemispherical headed 3.5 millimeter screws.

Substantially oval shaped apertures 64 are further configured and dimensioned so as to engage the head of a single substantially hemispherical headed 3.5 millimeter screw. The 3.5 millimeter screw has a head which is approximately 6 millimeters wide, and the 5 millimeter screw has a head which is approximately 8 millimeters wide.

Referring to FIG. 9, substantially oval shaped apertures 64 are provided with curved walls 66 so as to allow plate member 62 to be displaced in a direction either away from or towards the fracture site when a substantially hemispherical headed screw forcibly engages a curved wall 66 in an eccentric end of a substantially oval shaped aperture 64.

Plate member 62 is provided with narrow areas 68 disposed between substantially oval apertures 64 so as to facilitate the contouring of plate member 62 to match the contour of the fractured bone, and to provide a substantially constant amount of strength from the end of the substantially oval aperture 64 nearest the first end 63 to the end of the substantially oval aperture 64 nearest the second end 65.

Figure 8:
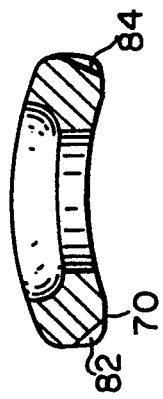
FIG. 8 is a cross-sectional view along line 8—8 of FIG. 6.
Figure 7:
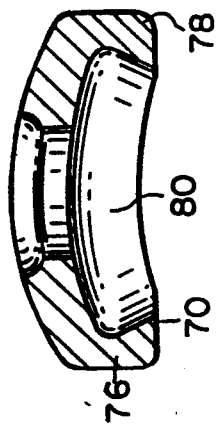
FIG. 7 is a cross-sectional view taken along line 7—7 of FIG. 6.
Figure 11:
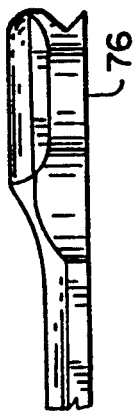
FIG. 11 is a side view of an end of a tibial plate according to the present invention.
Figure 10:
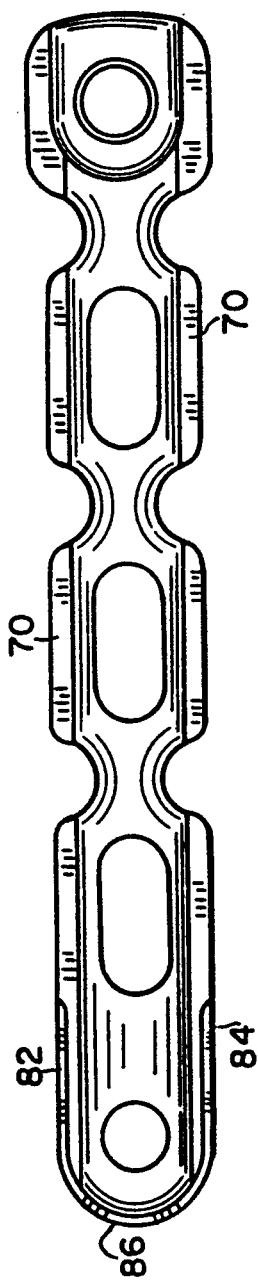
FIG. 10 is a bottom view of the tibial plate of FIG. 6.

As shown in FIGS. 7, 8 and 10, flat portions 70 are provided on the bottom side of plate member 62 along each of first side 67 and second side 69. Plate member 62 is provided with a slightly concave curvature between first side 67 and second side 69, excepting flat portions 70. The slightly concave curvature extends the length of plate member 62 from first end 63 to second end 65 and causes plate member 62 to resist rotational stresses when attached to a bone.

Plate member 62 is provided with a circular first connecting screw aperture 72 adjacent first end 63 and a circular second connecting screw aperture 74 adjacent second end 65. First connecting screw aperture 72 and second connecting screw aperture 74 are each provided with curved walls, as is shown in FIGS. 7 and 8.

First end 63 of body member 62 is provided with a first side beveled portion 82 and a second side beveled portion 84, each which extend a predetermined length from first end 63. Abutment beveled portion 86 is provided at first end 63 adjoining each of said first side beveled portion 82 and second side beveled portion 84. The width of the top side of plate member 62 in between first side beveled portion 82 and second side beveled portion 84 is the same as the width of plate member 62 at those portions which are provided with substantially oval apertures 64. The thickness from the top side to the bottom side of plate member 62 adjacent first end 63 remains constant from the portions provided with substantially oval apertures 64 through the portion provided with first side beveled portion 82 and second side beveled portion 84.

Second end 65 of plate member 62 is provided with a first side protrusion 76 and a second side protrusion 78, each which extend a predetermined length from said second end 65. Abutment protrusion 80 joins first side protrusion 76 and second side protrusion 78 and is spaced a predetermined length from said second end 65. First side protrusion 76, second side protrusion 78 and abutment protrusion 80 are configured and dimensioned so as to define a connecting C-shaped channel or cavity which can selectively removably engage and interlock with an end of a second plate member which is configured and dimensioned so as to correspond to the first end 63 of plate member 62 as detailed above.

Figure 12:
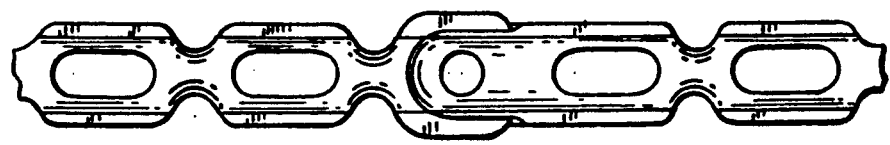
FIG. 12 is a bottom view of two tibial plates according to the present invention, each of which is selectively removably interlockingly engaged with the other at their respective ends without a connecting screw.

As shown in FIG. 12, when an end of a second plate member which is configured and dimensioned identically to the first end 63 of plate member 62, as detailed above, is disposed within the connecting C-shaped channel or cavity at second end 65 of plate member 62, first connecting screw aperture 72 of the second body member can be vertically aligned with second connecting screw aperture 74 of plate member 62 so that a straight bone screw can pass through first connecting screw aperture 72 of the second plate member and second connecting screw aperture 74 of plate member 62 so as to selectively removably engage plate member 62 with the second plate member.

The present invention comprises one bone plate with at least one means for selectively removable engagement with a second bone plate, and further comprises a plurality of bone plates each provided with at least one C-shaped channel for selectively removable engagement with another bone plate.

Figure 13:
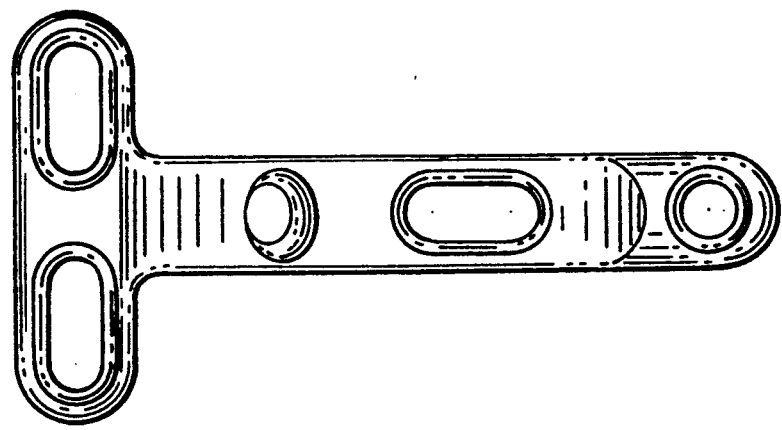
FIG. 13 is a top view of a T-shaped tibial plate according to the present invention.
Figure 14:
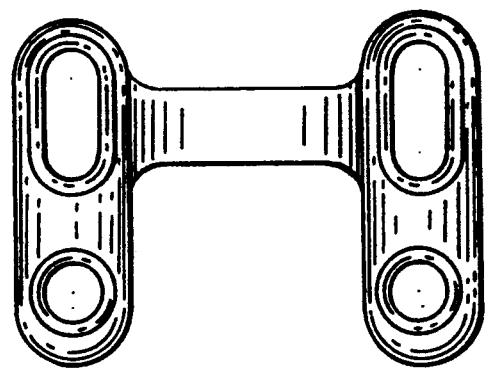
FIG. 14 is a top view of an H-shaped tibial plate according to the present invention.

The bone plates manufactured according to the present invention may be made of any length or shape or predetermined curvature, such as those illustrated in FIGS. 13 and 14. Each plate can be provided with a first and a second means for selectively removably engaging the plate with two other plates, or can be provided with only one means for selectively removably engaging the plate with one other plate, or can be provided with no such means as desired.

We claim:

1. A bone implant comprising a tab member having a proximal end and a distal end, the distal end of said tab member being configured to be removably engageable with the proximal end of an intramedullary rod which is properly disposed within an intramedullary canal of a bone and which has been inserted into said intramedullary canal through an implant incision in the flesh; means for removably engaging the proximal end of an intramedullary rod disposed at the distal end of said tab member; and having at least one bone screw aperture located proximally with respect to said engaging means and sufficiently close to the proximal end of said tab member so as to allow passage of a bone screw through said implant incision, through said bone screw aperture and into said bone when said tab member is removably engaged to the proximal end of said intramedullary rod.

2. The bone implant according to claim 1 further comprising an intramedullary rod having a proximal end configured to be removably engageable with the distal end of the tab member.

3. A method for implanting a bone implant comprising:
   a. providing an implant body member for insertion into a bone cavity, said body member having a proximal end and a distal end;
   b. providing an implant tab member having proximal and distal ends and at least one bone fixation aperture to allow for passage of a bone fixation screw for fastening said implant tab member to the bone, wherein the length of said tab member from said distal end to said proximal end varies at points around the periphery of said tab member to define a portion of shorter length as compared to other portions around the periphery and said least one bone fixation aperture is located to be accessible to insertion of said fixation screw by passing said screw proximally past said shorter length portion;
   c. providing means for selectively removably coupling said implant tab member distal end to said proximal end of said implant body member;
   d. providing a bone fixation screw;
   e. inserting said implant body member into a bone cavity through an opening in the flesh;
   f. inserting said implant tab member through said opening in the flesh and removably engaging the distal end of said implant tab member to the proximal end of said implant tab member;
   g. inserting said bone fixation screw through said opening in the flesh and through said bone fixation aperture in said implant tab member and into the bone.

4. The method for implanting a bone implant of claim 3 wherein said implant tab member is generally of an annular configuration and said shorter length portion of said implant tab member defines a bevelled end through which said bone fixation aperture is accessed.

5. The method for implanting a bone implant of claim 4 wherein said bone fixation aperture is disposed adjacent said bevelled end of said implant tab member.

6. A method for implanting a bone implant for fixing a fracture of a bone comprising:
   a. providing an elongated implant body member for insertion into the intramedullary canal of the bone, said implant body member having a proximal end and a distal end;
   b. providing an implant tab member having a proximal end portion and a distal end portion, said proximal end portion having a bevelled portion, at least one bone fixation aperture being located in said bevelled portion to provide means for easily accessing the inner side of the bone fixation aperture for the selective insertion of a bone fixation screw for fastening said implant tab member to the bone when said implant tab member is coupled to the proximal end of said implant body member when said implant body member is properly disposed within said bone cavity;
   c. providing means for selectively removably coupling said implant tab member to said proximal end of said implant body member;
   d. providing a bone fixation screw;
   e. inserting said implant body member through an opening in the flesh and into an intramedullary canal of a bone;
   f. inserting said implant tab member through said opening in the flesh and removably engaging the distal end of said implant tab member to the proximal end of said implant tab member;
   g. inserting said bone fixation screw through said opening in the flesh and through said bone fixation aperture in said implant tab member and into the bone.

7. A method for affixing a bone implant tab member to an intramedullary rod properly disposed within an intramedullary canal of a bone and which has been inserted into said intramedullary canal through an implant incision in the flesh comprising:
   a. providing a bone implant tab member being of generally annular configuration having a beveled proximal end and a distal end; said bone implant tab member having a bore in the distal end to allow for selectively removable engagement with a proximal end of an intramedullary rod; said bone implant tab member having at least one bone fixation aperture to allow for selective passage of a bone fixation screw for fastening said bone implant tab member to the bone; and said at least one bone fixation aperture being located in said bevelled proximal end of the bone implant tab member whereby said bone fixation aperture may be easily accessed through said implant incision when said bone implant tab member is fastened to the proximal end of an intramedullary rod properly disposed within an intramedullary canal;
   b. providing means for removably engaging the distal end of said bone implant tab member with the proximal end of an intramedullary rod;
   c. providing a bone fixation screw;
   d. inserting said bone implant tab member through said implant incision in the flesh and removably engaging the distal end of said implant tab member to the proximal end of the intramedullary rod;

e. inserting said bone fixation screw through said implant incision in the flesh, through the bone fixation aperture in said implant tab member and into the bone.

8. A method for implanting an intramedullary rod into an intramedullary canal of a bone comprising:
   a. providing an intramedullary rod for insertion into an intramedullary canal of a bone, said intramedullary rod having a bevelled proximal end, a distal end and a number of bone fixation apertures to allow for selective insertion of a bone fixation screw for fastening said intramedullary rod to the bone, at least one said bone fixation aperture being located in said bevelled proximal end whereby said bone fixation aperture may be easily accessed when said intramedullary rod is properly disposed within said intramedullary canal;
   b. providing a bone fixation screw;
   c. inserting said intramedullary rod through an incision in the flesh, through a proximal bone aperture communicating with the intramedullary canal and into the intramedullary canal of a bone;
   d. inserting said bone fixation screw through said incision in the flesh, through said bone fixation aperture located in said bevelled proximal end of said intramedullary rod and into the bone.

9. A method for proximal fixation of an intramedullary rod properly disposed within an intramedullary canal and which was inserted into the intramedullary canal through an implant incision in the flesh, which implant incision in the flesh was then closed comprising:
   a. providing an implant tab member having at least one bone fixation aperture and having proximal and distal ends; said bone fixation aperture configured and disposed so as to allow passage of a bone fixation screw through said implant incision in the flesh, when opened, through said bone fixation aperture and into the bone;
   b. providing means for removably engaging said distal end of said implant tab member to the proximal end of the intramedullary rod;
   c. providing a bone fixation screw;
   d. re-opening the incision in the flesh through which the intramedullary rod was inserted;
   e. inserting said implant tab member through said re-opened incision in the flesh and removably engaging the distal end of the implant tab member to the proximal end of the intramedullary rod;
   f. inserting said bone fixation screw through said re-opened incision in the flesh, through said bone fixation aperture and into the bone.

10. A method for implanting a bone implant comprising:
   a. making a proximal bone aperture in a bone, which proximal bone aperture communicates with the intramedullary canal of the bone and the surface of the proximal bone aperture forms a bevel with a plane perpendicular to the longitudinal axis of the intramedullary canal at the proximal bone aperture, thereby defining a bevelled bone portion;
   b. providing a bone implant for insertion into the intramedullary canal of a bone through said proximal bone aperture communicating with the intramedullary canal; said implant including a proximal end portion having at least one bone fixation aperture therein for insertion of a bone fixation screw for fastening said implant to the bone, said at least one bone fixation aperture being located sufficiently close to the proximal end of said implant to be accessible to insertion of said bone fixation screw by passage of said screw proximally of said bevelled bone portion into the bone fixation aperture when said implant is disposed within said intramedullary canal;
   c. providing a bone fixation screw;
   d. inserting said bone implant through said proximal bone aperture and into the intramedullary canal of the bone;
   e. inserting said bone fixation screw through said proximal bone aperture, through said bone fixation aperture and into the bone.

11. A method for proximal fixation of an intramedullary rod properly disposed within an intramedullary canal and which was inserted into the intramedullary canal through an implant incision in the flesh comprising:
   a. providing an implant tab member having proximal and distal ends and having at least one bone fixation aperture; said bone fixation aperture configured and disposed so as to allow passage of a bone fixation screw through said implant incision in the flesh, through said bone fixation aperture and into the bone;
   b. providing means for removably engaging said distal end of said implant tab member to the proximal end of the intramedullary rod;
   c. providing a bone fixation screw;
   d. inserting said implant tab member through said implant incision in the flesh and removably engaging the distal end of the implant tab member to the proximal end of the intramedullary rod;
   e. inserting said bone fixation screw through said implant incision in the flesh, through said bone fixation aperture and into the bone.

12. A method for proximal fixation of a bone implant disposed within a bone and which was inserted into the bone through an implant incision in the flesh comprising:
   a. providing an implant tab member having proximal and distal ends and having at least one bone fixation aperture; said bone fixation aperture configured and disposed so as to allow passage of a bone fixation screw through said implant incision in the flesh, when opened, through said bone fixation aperture and into the bone;
   b. providing means for removably engaging the distal end of said implant tab member to the proximal end of the bone implant;
   c. providing a bone fixation screw;
   d. inserting said implant tab member through said implant incision in the flesh and removably engaging the distal end of the implant tab member to the proximal end of the intramedullary rod;
   e. inserting said bone fixation screw through said implant incision in the flesh, through said bone fixation aperture and into the bone.

13. A method for implanting a bone implant comprising:
   a. making a proximal bone aperture in a bone, which proximal bone aperture communicates with the intramedullary canal of the bone and the surface of the proximal bone aperture forms a bevel with a plane perpendicular to the longitudinal axis of the intramedullary canal at the proximal bone aperture, thereby defining a bevelled bone portion;

b. providing a bone implant having proximal and distal ends for insertion into the intramedullary canal of a bone through said proximal bone aperture communicating with the intramedullary canal;

c. providing a bone implant tab member having proximal and distal ends and having at least one bone fixation aperture therein for insertion of a bone fixation screw for fastening said bone implant tab member to the bone, said at least one bone fixation aperture being located sufficiently close to the proximal end of said bone implant tab member to be accessible to insertion of said bone fixation screw by passage of said screw proximally of said bevelled bone portion into the bone fixation aperture when bone said implant tab member is fastened to the proximal end of said bone implant and said bone implant is disposed within said intramedullary canal;

d. providing a bone fixation screw;

e. providing means for removably engaging the distal end of said bone implant tab member with the proximal end of said bone implant;

f. inserting said bone implant through said proximal bone aperture and into the intramedullary canal of the bone;

g. inserting said bone implant tab member through said proximal bone aperture and fastening the distal end of said bone implant tab member to the proximal end of said bone implant;

h. inserting said bone fixation screw through said proximal bone aperture, through said bone fixation aperture and into the bone.

14. A method for implanting a bone implant according to claim 13 wherein said bone implant is an intramedullary rod.

15. A method for implanting a bone implant according to claim 14 wherein said bone is a tibia.

16. A bone implant tab member for proximal fixation of an intramedullary rob properly disposed within an intramedullary canal and which intramedullary rod was inserted into the intramedullary canal through an implant incision in the flesh comprising:

an implant tab member having proximal and distal ends and having at least one bone fixation aperture; said bone fixation aperture configured and disposed so as to allow passage of a bone fixation screw through said implant incision in the flesh, through said bone fixation aperture and into the bone; and means for removably engaging the distal end of said implant tab member to the proximal end of the intramedullary rod wherein said bone fixation aperture is disposed proximally with respect to said means.

* * * * *